United States Patent
Hoeg et al.

(10) Patent No.: US 7,517,314 B2
(45) Date of Patent: Apr. 14, 2009

(54) ENDOSCOPIC IMAGING WITH INDICATION OF GRAVITY DIRECTION

(75) Inventors: Hans David Hoeg, Arcadia, CA (US); Eric Lawrence Hale, Altadena, CA (US); Nathan Jon Schara, Pasadena, CA (US)

(73) Assignee: Karl Storz Development Corp., Goleta, CA (US)

( * ) Notice: Subject to any disclaimer, the term of this patent is extended or adjusted under 35 U.S.C. 154(b) by 613 days.

(21) Appl. No.: 11/055,444

(22) Filed: Feb. 10, 2005

(65) Prior Publication Data

US 2006/0084840 A1   Apr. 20, 2006

Related U.S. Application Data

(60) Provisional application No. 60/618,618, filed on Oct. 14, 2004.

(51) Int. Cl.
*A61B 1/00* (2006.01)

(52) U.S. Cl. .................................. 600/117; 600/173
(58) Field of Classification Search ................ 600/117, 600/118, 109, 112, 173; 348/65, 74
See application file for complete search history.

(56) References Cited

U.S. PATENT DOCUMENTS

| | | | | |
|---|---|---|---|---|
| 5,179,656 | A * | 1/1993 | Lisle | 715/836 |
| 5,280,781 | A * | 1/1994 | Oku | 600/114 |
| 5,307,804 | A | 5/1994 | Bonnet | 126/7 |
| 5,881,321 | A * | 3/1999 | Kivolowitz | 396/53 |
| 5,899,851 | A | 5/1999 | Koninckx | 600/117 |
| 6,097,423 | A | 8/2000 | Mattsson-Boze et al. | 348/65 |
| 6,144,382 | A * | 11/2000 | Hill | 345/619 |
| 6,263,230 | B1 * | 7/2001 | Haynor et al. | 600/424 |
| 6,471,637 | B1 | 10/2002 | Green et al. | 600/109 |
| 6,522,906 | B1 | 2/2003 | Salisbury, Jr. et al. | |
| 6,542,824 | B1 * | 4/2003 | Berstis | 701/220 |
| 6,573,896 | B1 * | 6/2003 | Ribadeau Dumas et al. | 345/473 |
| 6,902,528 | B1 * | 6/2005 | Garibaldi et al. | 600/118 |
| 7,211,042 | B2 * | 5/2007 | Chatenever et al. | 600/117 |
| 2002/0161280 | A1 | 10/2002 | Chatenever et al. | 600/112 |
| 2004/0127769 | A1 | 7/2004 | Hale et al. | |
| 2005/0154260 | A1 | 7/2005 | Schara et al. | 600/117 |
| 2005/0228230 | A1 | 10/2005 | Schara et al. | 600/171 |
| 2006/0036162 | A1 * | 2/2006 | Shahidi et al. | 600/424 |

FOREIGN PATENT DOCUMENTS

EP    1466552 A1    10/2004

(Continued)

OTHER PUBLICATIONS

Extended European Search Report, Jun. 22, 2006, 7 Pages.

*Primary Examiner*—John P Leubecker
(74) *Attorney, Agent, or Firm*—St. Onge Steward Johnston & Reens LLC

(57) ABSTRACT

A method for presenting an indicator of the upright orientation of an endoscopic image. An electronic rotation pick-up means is fixed to the housing of an endoscope. The electronic rotation pick-up means produces signals indicating rotations of the endoscope. A microprocessor uses these signals to calculate the difference between the upright image orientation and the actual image orientation. The calculation includes factors to account for endoscope roll, endoscope pitch, and endoscope viewing direction. The upright indicator is displayed on a video display device along with the endoscopic image.

13 Claims, 5 Drawing Sheets

FOREIGN PATENT DOCUMENTS

| | | | |
|---|---|---|---|
| JP | 03118019 A | * | 5/1991 |
| JP | 06269403 A | * | 9/1994 |
| JP | 10262921 A | * | 10/1998 |
| WO | 9846120 A2 | | 10/1998 |

* cited by examiner

ENDOSCOPIC IMAGING WITH INDICATION OF GRAVITY DIRECTION

CROSS-REFERENCE TO RELATED APPLICATIONS

This application claims the benefit of U.S. provisional application Ser. No. 60/618,618 filed on Oct. 14, 2004, entitled "Endoscopic Imaging with Indication of Gravity Direction", the contents of which are incorporated herein by reference.

STATEMENT REGARDING FEDERALLY SPONSORED RESEARCH

Not Applicable

FIELD OF THE INVENTION

The present invention relates to endoscopic imaging, and in particular to endoscopic image orientation and its relationship to the direction of gravity and the viewer's reference frame.

BACKGROUND OF THE INVENTION

An endoscope is an elongated tubular structure which is inserted into body cavities to examine them. The endoscope includes a telescope with an objective lens at its distal end. The telescope usually includes an image-forwarding system. In rigid endoscopes it is a series of spaced-apart lenses. In flexible endoscopes it is a bundle of tiny optical fibers assembled coherently to forward the image. Some endoscopes include a camera means, such as a CCD or CMOS image sensor, in the distal portion and forward the image electronically. This invention is applicable to all types of image forwarding systems.

Many endoscopes view only directly forward. Others feature fixed or movable reflectors in the distal portion to allow off-axis viewing. Some, most commonly flexible types, feature actuated bending portions at the distal end. This invention is applicable to all types of axial, non-axial, and variable direction of view endoscopes.

At the proximal end of the image-forwarding system, some endoscopes include an ocular lens which creates a virtual image for direct human visualization. Often a camera means, such as a CCD or CMOS chip, is connected to the endoscope. It receives the image and produces a signal for a video display. Some endoscopes have a camera means built directly into the endoscope.

While surgeons can, and often do, look directly into the endoscope through an ocular lens, it has become more common for them to use an attached video camera and observe an image on a video screen. In a surgical or diagnostic procedure, the surgeon manipulates the endoscope. He may cause it to pitch about a lateral axis or roll about a longitudinal axis. As these manipulations occur to an endoscope with an attached camera, the camera faithfully relates what it sees, with its own upright axis displayed as the upright axis of the image on the display. This often results in rotation of the viewed image.

That is the very problem. As the image rotates, the surgeon loses track of what is actually up and down inside the endoscopic cavity. This disorientation is one of endoscopy's greatest enemies and has lead to severe mistakes such as the snipping of optical nerves which during a procedure were believed to be a different part of the anatomy. When surgical procedures where open rather than endoscopic, the surgeon could see the anatomy directly and therefore did not have a disorientation problem. However, during an endoscopic procedure the surgeon's viewpoint is different from the viewpoint of the endoscope, and the surgeon must continuously try to correlate his own mental picture of the anatomy with the endoscopic picture on the display. In doing this, the need to know what is up and down inside the endoscopic cavity is so strong that it has become common for surgeons to observe the flow direction of fluid droplets on the endoscope cover window or search for pooling blood in order to get a sense of direction inside the cavity. Aside from being important for distinguishing anatomical features which may look similar, knowing the up-direction also helps in understanding the endoscope's position relative to the surrounding anatomy. Ideally, the surgeon would be able to relate to the endoscopic cavity as if his own eyes were actually inside the cavity.

An attempted solution to this problem is proposed in U.S. Pat. No. 5,307,804 to Bonnet (1994), which is incorporated herein by reference in its entirety. An object of this invention was to maintain the orientation of an endoscopic image without the use of electronic sensing and positioning devices. A pendulum fixed to a camera is rotatably attached to an endoscope. The pendulum maintains an orientation with respect to gravity around the endoscope longitudinal axis. As the endoscope rotates, the pendulum causes the camera to rotate in the opposite direction relative to the endoscope. This is intended to maintain the image in a proper orientation.

An endoscope with rotational orientation correction is also suggested in U.S. Pat. No. 5,899,851 to Koninckx (1999), which is incorporated herein by reference in its entirety. An electronic rotation pick-up means responsive to gravity senses rotation of a camera around the endoscope longitudinal axis. An image rotator rotates the camera image according to the rotation signal from the rotation pick-up means.

Another endoscope and camera system with rotational orientation correction is disclosed in U.S. Pat. No. 6,097,423 to Mattsson-Boze, et al. (2000), which is incorporated herein by reference in its entirety. Electronic sensing and positioning devices combine to sense and correct the rotation of a camera rotatably attached to an endoscope. An accelerometer fixed to the camera serves as an electronic rotation pick-up means responsive to gravity. A motor rotates the camera according to signals from the accelerometer. This accelerometer and motor system is functionally equivalent to the pendulum described by Bonnet. While the pendulum relies on the force of gravity to rotate, the accelerometer sensitively measures gravity and the motor rotates the assembly accordingly. The system can therefore be thought of as an electro mechanical pendulum. Mattsson-Boze also recognizes rotation of the image by electronic manipulation to correct the image orientation, but actively discourages this practice for several reasons.

U.S. Pat. No. 6,471,637 to Green, et al. (2002), which is incorporated herein by reference in its entirety, discloses the same apparatus as disclosed in Mattsson-Boze, and suggests two alternative methods for image rotation. In the first method, an optical image rotator is used instead of a rotating camera. In the second method, electronic manipulation is used to correct the image orientation. Also, one or more gyroscopes are suggested as alternative electronic rotation pick-up means.

U.S. patent application Ser. No. 2002/0161280 by Chatenever, et al. which is Incorporated herein by reference in its entirety, discloses the same apparatus as disclosed in Mattsson-Boze and in Green, and suggests two alternative methods for electronic rotation pick-up. In the first method, image analysis is used to compute a rotational signal. In the second method, a machine vision system is used to compute a rotation signal.

U.S. Patent Application Nos. 2005/0228230 and 2005/0154260 by Schara et al., which are incorporated herein by reference in their entirety, teach general solutions to the image orientation problem. Unlike the above disclosures, these disclosures can provide a gravity-leveled endoscopic image for all scope types and configurations, regardless of endoscope pitch and roll and any line of sight offset from the axis of the endoscope.

All of the above solutions teach only automatic reorienting and leveling of the endoscopic image. From market surveys and discussions with surgeons in different disciplines it has become apparent that even just an indicator of vertical without reorientation of the endoscopic image would be very useful. Surgeons have become accustomed to reorienting the endoscopic camera manually during a procedure and do not necessarily require or even want the image automatically corrected for them. Simply providing an indicator of vertical would allow the surgeons to keep the practice of adjusting the camera themselves and at the same time give a visual key of how much the camera must be rotated in order to achieve a truly upright image. Alternately, the surgeon could elect to maintain a current camera orientation but would with an indicator at least be able to see which direction was up. This is especially relevant with the latest chip-in-tip endoscopes which have a distal camera that cannot be rotated.

Also, except for U.S. Patent Applications Nos. 2005/0228230 and 2005/0154260 by Schara et al, all of the above solutions compensate only for roll about the longitudinal axis, and provide a rotationally corrected image only for axial viewing endoscopes. They provide an approximation of the correct orientation for slightly oblique viewing endoscopes held near horizontal, but only Schara et al. teach a solution that is correct for straight, oblique, side, retro, and variable direction of view endoscopes. The current practice in endoscopy is for the surgeon to try to keep the image vertical by rotating the proximal camera head such that its roll about the endoscope axis stays level with the horizon. This is done regardless of the type of scope being used, whether straight, oblique, or flexible. The widespread misunderstanding here is that this practice keeps the image leveled. It in fact only provides a leveled image in the case of a rigid straight viewing endoscope. For any other scope type this practice does not provide a leveled image and is misleading because what is believed to be a leveled image actually is not.

Thus, it is an object of this invention to provide an indicator of the correct upright orientation (with respect to the viewer) of a viewed image from an endoscope. It is an additional object of this invention to be applicable to any axial, oblique, side, or retro viewing endoscope as well as any endoscope with a variable direction of view.

BRIEF SUMMARY OF THE INVENTION

According to a feature of this invention an electronic rotation pick-up means is fixed to the housing of an endoscope. The electronic rotation pick-up means produces signals indicating rotations of the endoscope. A microprocessor uses these signals to calculate a rotational indicator for the endoscopic view orientation. The calculation includes factors to account for endoscope roll, endoscope pitch, and endoscope viewing direction. The indicator is displayed on a video display device. With this arrangement the indicator shows which direction is up and how much the current image orientation is off from vertical or how much the user must rotate the camera in order to make the image "upright" on the display, as though viewed by a surgeon standing or sitting in an upright position.

The invention includes a method for indicating the proper upright orientation (with respect to the viewer) of an image from an endoscope comprising calculating the upright direction, wherein said calculating comprises accounting for the effects on image orientation caused by endoscope pitch, endoscope roll, and endoscope direction of view; and presenting an indication of said proper upright orientation.

DETAILED DESCRIPTION OF THE INVENTION

Figure 1:
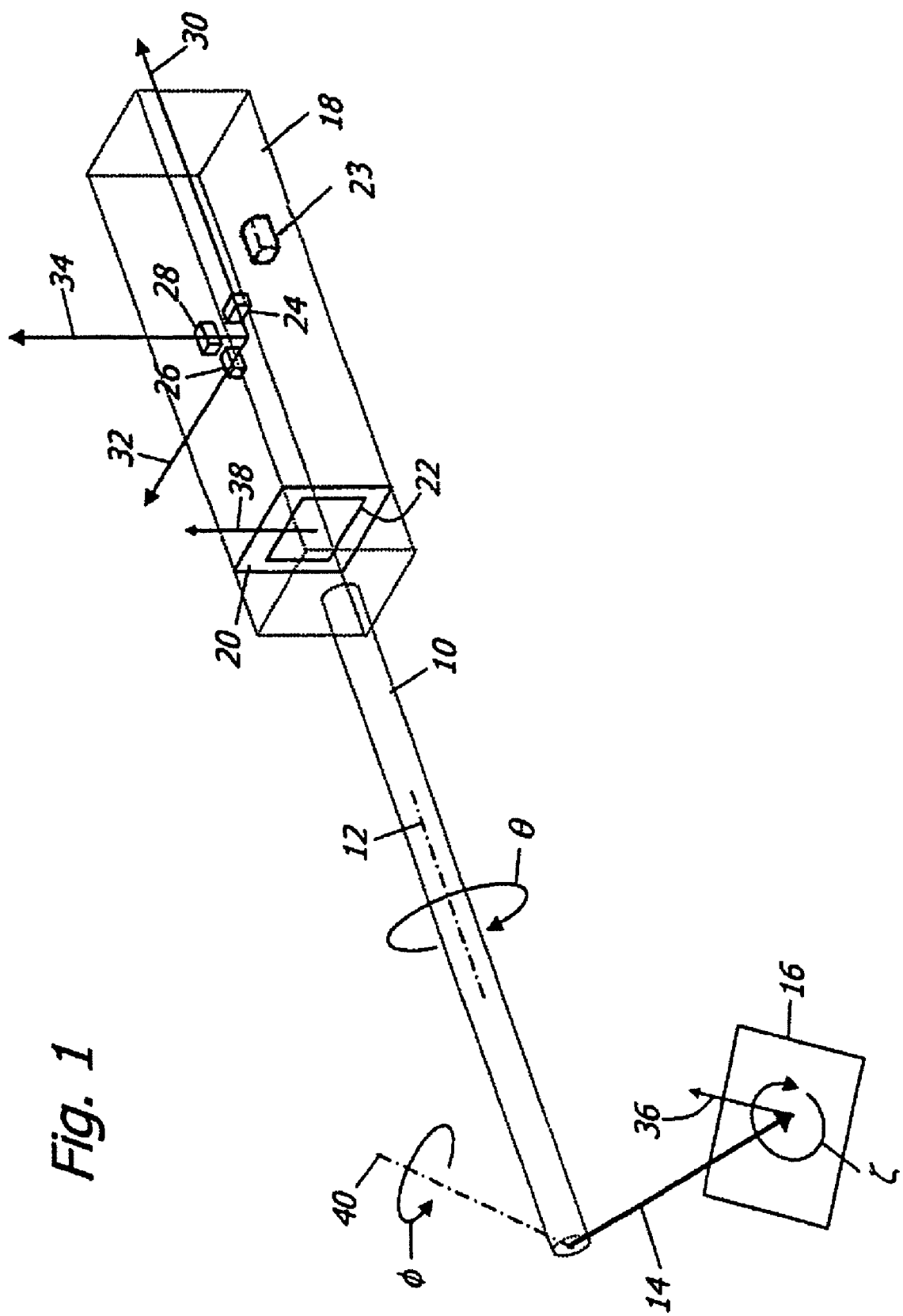
FIG. 1 is a schematic view of an endoscope useful with this invention.

FIG. 1 schematically shows an endoscope. The endoscope includes a shaft 10 that contains elements that are conventionally provided. The shaft has a longitudinal axis 12.

An objective optical system is provided at the distal end of the shaft to give the endoscope a view vector 14 and a field of view 16. The objective optical system comprises components such as lenses, prisms, reflectors, etc. The objective optical system may be adjustable or mounted adjustably to provide a variable direction of view.

A housing 18 is provided at the proximal end of the shaft 10. An image sensing device or camera 20 is mounted in the housing 18. It is configured to receive images 22 from the objective optical system. The housing 18 encases an electronic microprocessor 23 for performing calculations.

Electronic rotation pick-up means, in the preferred embodiment three accelerometers 24, 26, 28 responsive to gravity, are mounted to the housing 18. Each accelerometer measures a component of gravity along a particular measurement axis. The accelerometers provide pulse-width-modulated signals to the processor which can convert each signal into a gravitational force measurement. Changes in the gravitational force measurements from the accelerometers are related to rotations of the endoscope.

In order to adequately describe the method of the current invention, an appropriate mathematical framework needs to be defined.

The housing 18 has a longitudinal axis 30 and a lateral axis 32 which are horizontal when the housing is in its upright position, and an upright axis 34 which is vertical when the housing is in its upright position. These axes 30, 32, 34 are orthogonal. Each accelerometer axis is aligned with an axis of the housing 18. The first accelerometer 24 measures a component of gravity along the longitudinal axis 30. The second accelerometer 26 measures a component of gravity along the lateral axis 32. The third accelerometer 28 measures a component of gravity along the upright axis 34. The force from the longitudinal accelerometer 24 is Z. The force from the lateral accelerometer 26 is X. The force from the upright accelerometer 28 is Y.

The endoscope has a view vector 14. The camera upright projection 36 is the projection of the default upright axis 38 of the camera 20 through the optics and along the view vector 14.

A view vector pivot axis 40 is defined at the distal end of the endoscope, initially aligned with the housing upright axis 34. The pivot axis 40 may or may not exist in the actual implementation of the endoscope, but is defined as part of the mathematical framework. The pivot axis 40 may be realigned by rotating it about the longitudinal axis 12. The variable theta is used to describe the angle of the pivot axis 40 relative to the upright axis 34 as rotated about the longitudinal axis 12. The variable phi is used to describe the angle of the view vector 14 relative to the longitudinal axis 12 as rotated about the pivot axis 40. The variable zeta is used to describe the angle of the camera upright projection 36 relative to the pivot axis 40 as rotated about the view vector 14. It should be noted that the above parameterization uses ZYZ Euler angles, which are commonly used to describe three dimensional rotations.

For simple oblique, side, or retro viewing endoscopes, the above parameterization variables theta, phi, and zeta will be fixed constants defined for each endoscope. Variable direction of view endoscopes require that one or more of the variables change during operation to reflect the changing direction of view.

Figure 2:
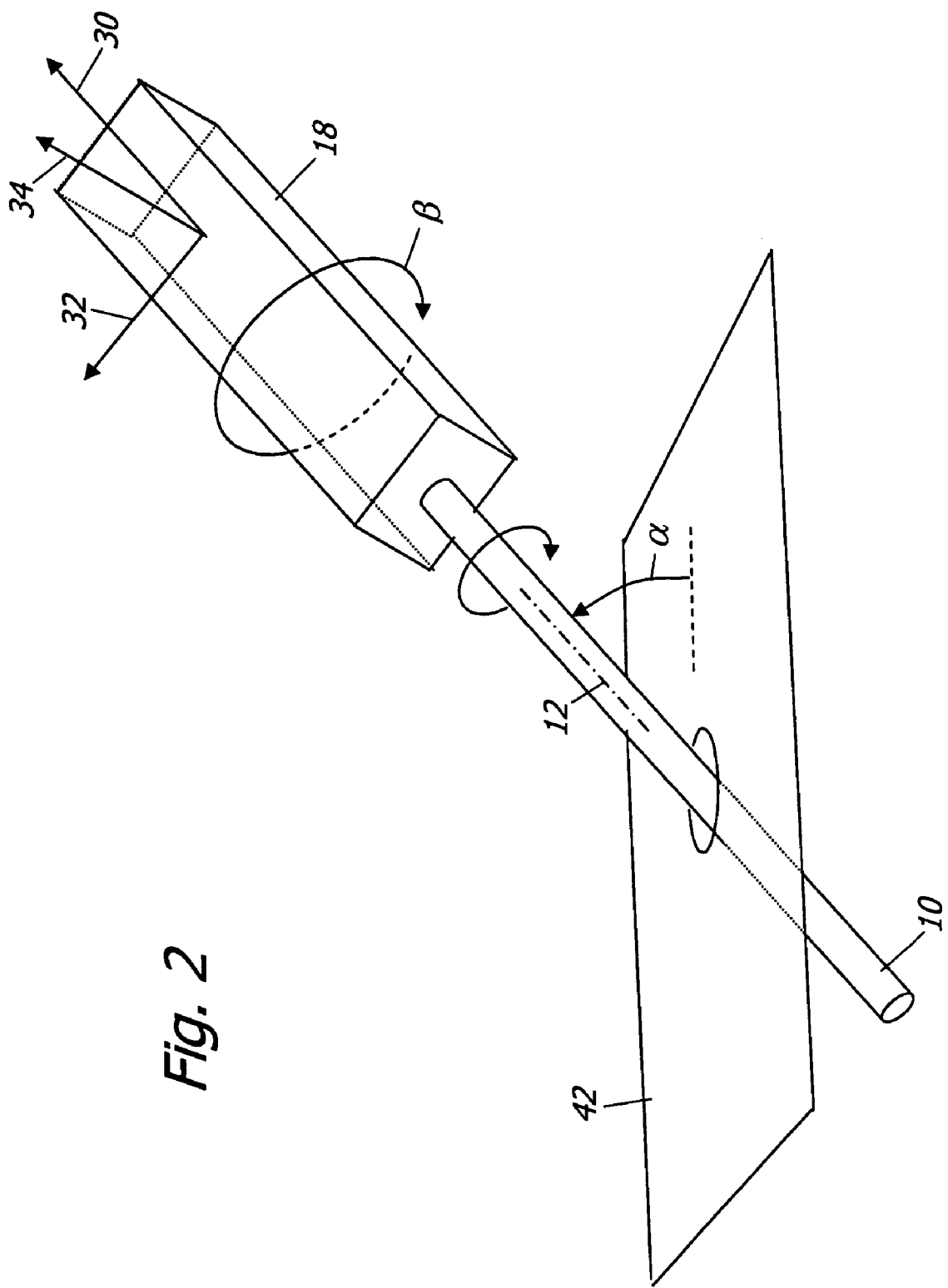
FIG. 2 illustrates endoscope attitude.

During use, the endoscope will be positioned with an attitude as shown in FIG. 2. The attitude is parameterized as pitch and roll. The variable alpha is used to describe the pitch angle of the longitudinal axis 12 relative to horizontal 42. The variable beta is used to describe the roll angle of the endoscope about its longitudinal axis 12. Both pitch and roll may be adjusted during use.

The microprocessor calculates pitch and roll from the accelerometer outputs according to the formulas:

$$\beta = \arctan\frac{X}{Y} \qquad \alpha = \arctan\frac{Z}{Y/\cos\beta}$$

Figure 3:
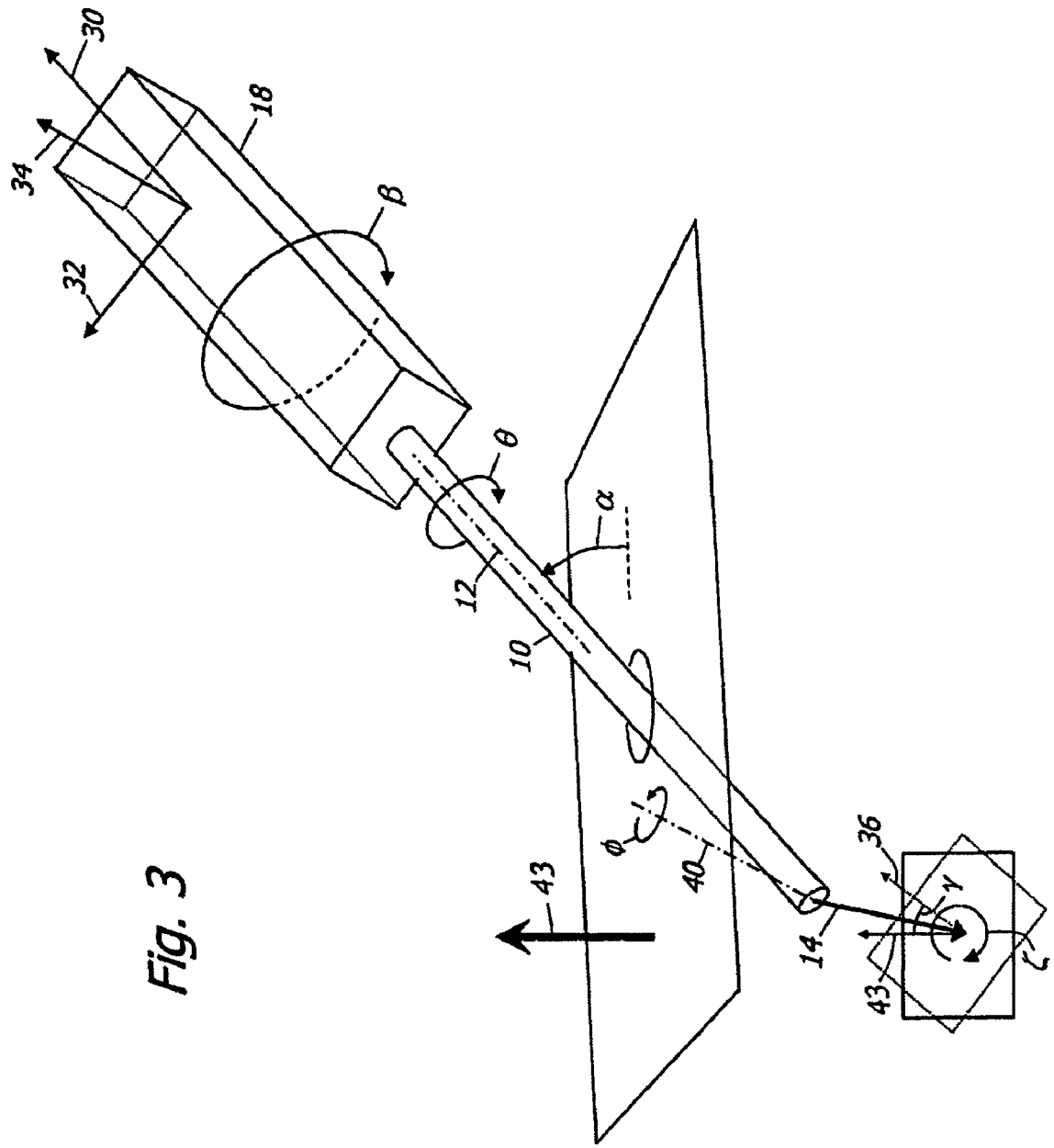
FIG. 3 shows the angular amount by which the endoscopic image is off the gravity upright direction.

As shown if FIG. 3, the camera upright projection 36 is offset from gravity upright 43 by a correction angle. The variable gamma is used to describe the correction angle as a rotation about the view vector 14. The microprocessor calculates gamma according to the formula:

$$\gamma = -\zeta - \arctan\frac{-\sin\alpha\sin\phi + \cos\alpha\cos\phi\sin(\beta+\theta)}{\cos\alpha\cos(\beta+\theta)}$$

Figure 4:
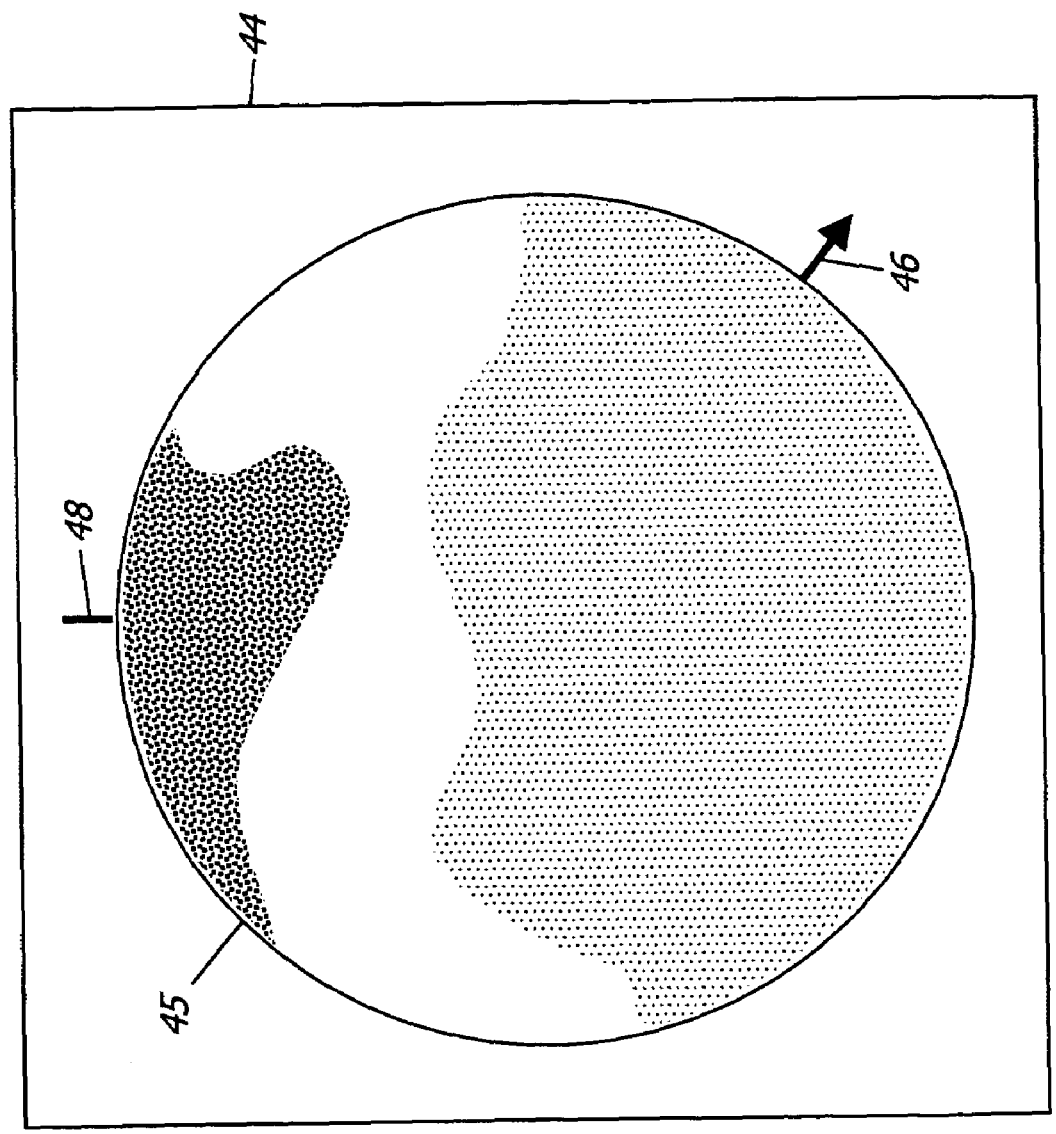
FIG. 4 shows a displayed endoscopic image with an indicator of the upright direction.

A video display 44 is used to provide the endoscopic image 45 along with an upright direction indicator 46 to the user, as shown in FIG. 4. The indicator 46 is in this embodiment a direction arrow, but it could be any type of graphic object such as a dot or a line. An optional vertical stripe 48 indicates the physical top of the display 44 and provides a reference point for rotating the camera. If the user wants to arrange the endoscopic image 45 such that its up-direction is aligned with the up-direction of the display 44, he can rotate the camera (or image itself if the system has some other means of image rotation) until the indicator 46 lines up with the stripe 48. The video display 44 may be any device suitable for displaying images from the endoscope.

Figure 5B:
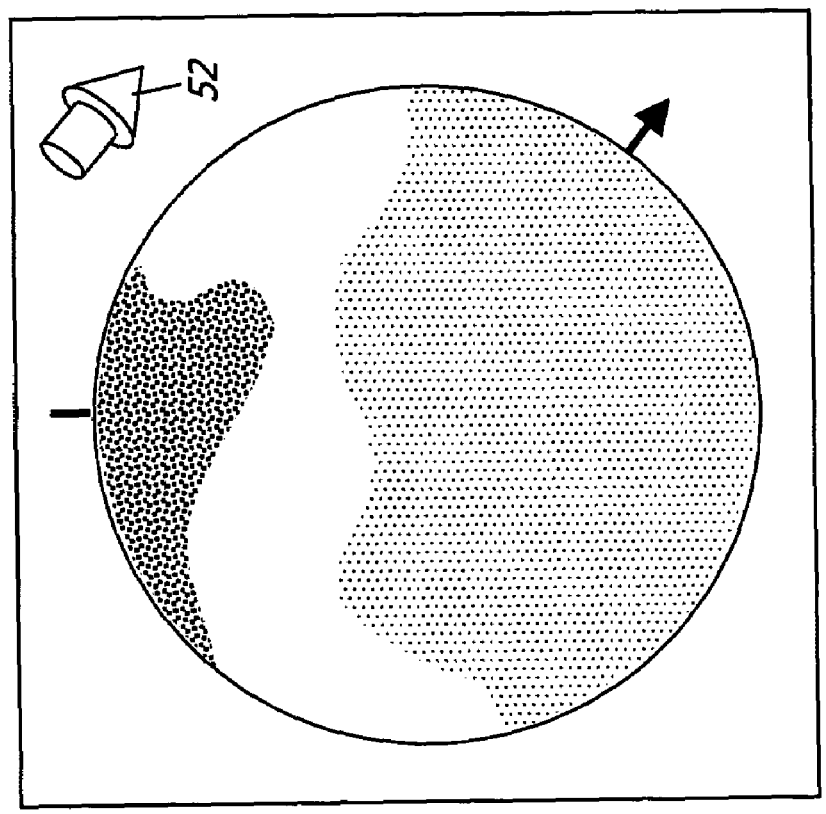
FIGS. 5A and 5B illustrate a displayed endoscopic image including additional indicators providing information about the endoscope attitude.
Figure 5A:
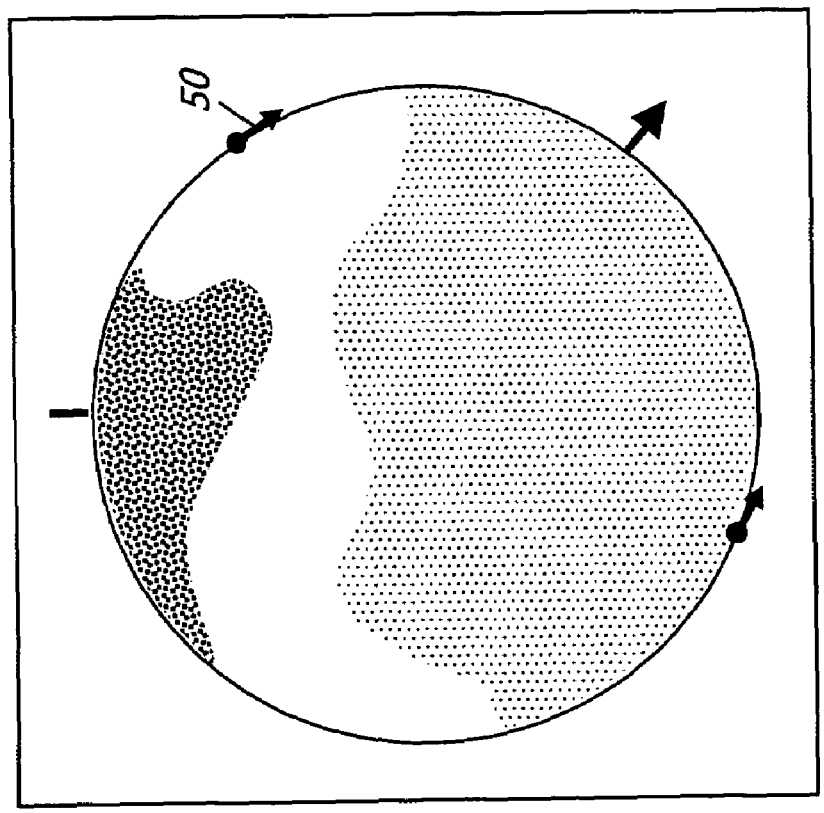

Along with the image orientation indicator 46, an additional set of indicators 50 could be used to give the user a sense of the endoscope's orientation, as shown in FIG. 5A. In this case these indicators 50, which slide along the perimeter of the image 44, indicate whether the endoscope is pointing away from the user or towards the user. Alternately, a 3D arrow indicator 52 can used (FIG. 5B).

In an alternative embodiment, one or more gyroscopes can be used as the electronic rotation pick-up means. The gyroscope output is used to determine the attitude of the endoscope. A gyroscope creates a signal representative of a force proportional to the angular displacement relative to its axis of rotation. Methods of determining attitude using gyroscopes are described in Chatenever, but the details of these methods are not necessary for an understanding of this invention.

In a further embodiment of the present invention, a machine vision system is used to compute the attitude of the endoscope. In such a system, the endoscope has thereon or therein at least one signal emitting element which emits some form of energy which is received by a receiver located at some location remote from the endoscope, such is in the ceiling of the operating room, mounted on a tripod or the like, or in a wall. By analyzing the energy received from the signal emitting elements, the receiver calculates the attitude of the endoscope. The signal emitting elements may themselves generate the energy, such as in the case of light emitting diodes, magnets, or the like, or may comprise reflectors for reflecting energy emitted from some transmitting source located at some location remote from the endoscope, such is in the ceiling of the operating room, mounted on a tripod or the like, or in a wall. The Transmitting source thus transmits energy, which is reflected off the signal emitting elements, and is received by the receiver. The energy may comprise, for example, infrared energy, light in the visual spectrum, magnetic energy, or the like.

The present invention has been described above in terms of a presently preferred embodiment so that an understanding of the present invention can be conveyed. However, there are many alternative arrangements for a method for providing gravity referenced endoscopic imaging not specifically described herein but with which the present invention is applicable. For example, and alternative mathematical framework describing the endoscope will lead to an alternative formula for the upright orientation calculation. Also, there are many different ways to indicate the upright direction. In addition, while the examples were given with respect to endoscopes for use in surgical procedures, the present invention is equally applicable with respect to borescopes or the like for use within various mechanical structures. Therefore, the term "endoscope" as used herein, refers to an endoscope (used for medical procedures) or any similar device such as a borescope, a fiberscope, etc.

This invention is not to be limited by the embodiments shown in the drawings and described in the description, which are given by way of example and not of limitation, but only in accordance with the scope of the appended claims.

We claim:

1. A system for indicating the proper upright orientation of images, comprising:
    a scope for acquiring images, said scope having a view vector, a longitudinal axis, and a view vector pivot axis angularly offset from the longitudinal axis about which the view vector pivots;
    at least three rotation sensors for monitoring rotation of said scope about three substantially orthogonal axes and generating signals therefor;
    a processor connected to said rotation sensor that receives the signals and calculates an image upright direction based thereon; and
    a display device connected to said scope for displaying the acquired images, wherein the display device displays with the images a graphical representation of a three-dimensional indicator of the calculated image upright direction based on the rotation of said scope relative to each of the three substantially orthogonal axes;

wherein the calculated upright direction is further based on the pivoting of the view vector relative to the longitudinal axis of said scope.

2. The system of claim 1, wherein said rotation sensors comprise accelerometers.

3. The system of claim 1, wherein said rotation sensors comprise at least one gyroscope.

4. The system of claim 1, wherein the graphical representation comprises a graphical representation of a three-dimensional arrow.

5. A method for indicating the proper upright orientation of images, comprising:

acquiring images with a scope having a view vector, a longitudinal axis, and a view vector pivot axis angularly offset from the longitudinal axis about which the view vector pivots;

monitoring rotation of said scope about three substantially orthogonal axes;

calculating an image upright direction based on the rotation of said scope about the three substantially orthogonal axes and the pivoting of the view vector relative to the longitudinal axis of said scope;

displaying the acquired images on a display device; and displaying with the images a graphical representation of a three-dimensional indicator of the calculated image upright direction based on the rotation of said scope relative to each of the three substantially orthogonal axes.

6. The method of claim 5, wherein the graphical representation comprises a graphical representation of a three-dimensional arrow.

7. The method of claim 5, wherein the step of monitoring rotation of the scope comprises using at least three accelerometers to measure the rotation of the scope about three substantially orthogonal axes.

8. The method of claim 5, wherein the step of monitoring rotation of the scope comprises using at least one gyroscope to measure the rotation of the scope about three substantially orthogonal axes.

9. A method for indicating the proper upright orientation of images, comprising:

providing a scope having a view vector, a longitudinal axis, and a view vector pivot axis angularly offset from the longitudinal axis about which the view vector pivots;

acquiring images with the scope;

monitoring rotation of said scope about three substantially orthogonal axes;

calculating an inclination of the view vector as the view vector pivots relative to the longitudinal axis of the scope, wherein said calculating comprises accounting for the effects on the orientation of the images caused by rotation about the three substantially orthogonal axes;

displaying the inclination of the view vector with the acquired images on a display device.

10. The system of claim 9, wherein the step of monitoring rotation of the scope comprises using at least three accelerometers to measure the rotation of the scope about three substantially orthogonal axes.

11. The system of claim 9, wherein the step of monitoring rotation of the scope comprises using at least one gyroscope to measure the rotation of the scope about three substantially orthogonal axes.

12. The method of claim 9, wherein the step of displaying the inclination of the view vector comprises displaying at least one marker around the edge of said endoscopic image.

13. The method of claim 9, wherein the step of displaying the inclination of the view vector comprises displaying; a pointer adjacent to said endoscopic image.

* * * * *